US00PP31791P2

(12) United States Plant Patent
Lim

(10) Patent No.: US PP31,791 P2
(45) Date of Patent: May 26, 2020

(54) ***ROSA HYBRIDA* PLANT NAMED 'LIMFORMOSA'**

(50) Latin Name: *Rosa hybrida*
Varietal Denomination: LIMformosa

(71) Applicant: Altman Specialty Plants, Inc, Vista, CA (US)

(72) Inventor: Peter Lim, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 16/350,557

(22) Filed: Nov. 30, 2018

(51) Int. Cl.
*A01H 5/02* (2018.01)
*A01H 6/74* (2018.01)

(52) U.S. Cl.
USPC ..... Plt./107
CPC ..... *A01H 6/749* (2018.05)

(58) Field of Classification Search
USPC ..... Plt./107
See application file for complete search history.

*Primary Examiner* — Anne Marie Grunberg
(74) *Attorney, Agent, or Firm* — Cassandra Bright

(57) ABSTRACT

A new and distinct cultivar of shrub rose plant named 'LIMformosa' is disclosed, characterized by distinctive fully double medium to dark pink flowers with a moderately strong rose fragrance. Plants are vigorous and can be grown on their own roots. Flowers drop petals cleaning after bloom is spent. Plants flower continuously and exhibit good resistance to blackspot diseases. The new variety is a *Rosa*, normally produced as an outdoor garden or container plant.

1 Drawing Sheet

Latin name of the genus and species: *Rosa hybrida.*
Variety denomination: 'LIMformosa'.

BACKGROUND OF THE INVENTION

The new *Rosa* cultivar is a product of a planned breeding program conducted by the inventor, Peter Ping Lim. The objective of the breeding program was to produce vigorous new garden shrub rose varieties for ornamental commercial applications. The cross resulting in this new variety was made during May of 2009.

The seed parent is the unpatented variety *Rosa* 'BNIf1'. The pollen parent is the variety *Rosa* 'BAIgirl', U.S. Pat. No. 19,952. The new variety was selected in 2010 by the inventor in a group of seedlings resulting from the 2009 crossing, in a research nursery in McMinnville, Oreg.

At the time of this filing plants of 'LIMformosa' have not been publicly released. The first sale is projected for March of 2019 in the United States. Information about the new variety was published in *Nurseryman Management* Magazine May of 2018. This publication, however, was not accompanied by any public access to plant material.

Asexual reproduction of the new cultivar was performed by vegetative cuttings. This was first performed at a research greenhouse in McMinnville, Oreg. in June 2010 and has shown that the unique features of this cultivar are stable and reproduced true to type in more than 5 successive generations.

SUMMARY OF THE INVENTION

The cultivar 'LIMformosa' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LIMformosa' These characteristics in combination distinguish 'LIMformosa' as a new and distinct *Rosa* cultivar:

1. Large, vigorous, shrub type rose with a large hybrid tea rose type flower.
2. Petals drop clean when done blooming.
3. Moderately strong rose fragrance.
4. Resistance to black spot disease.
5. Can be grown without grafting, performs vigorously on its own roots.

Plants of the new cultivar 'LIMformosa' are similar to plants of the seed parent, in most horticultural characteristics, however, plants of the new cultivar 'LIMformosa' differ in the following:

1. New variety's flowers are a pink blush color; seed parent's flowers are light yellow.

Plants of the new cultivar 'LIMformosa' are similar to plants of the pollen parent in most horticultural characteristics, however, plants of the new cultivar 'LIMformosa' differs in the following;

1. The new variety has 50 to 80 petals per flower, the pollen parent has about 30 petals typically.
2. The new variety has a strong, peppery scented flower, the pollen parent is only slightly scented.

COMMERCIAL COMPARISON

Plants of the new cultivar 'LIMformosa' can be compared to the commercial variety *Rosa* 'Belinda's Dream', unpatented. These varieties are similar in most horticultural characteristics, however 'LIMformosa' differs in the following:

1. Flowers of this comparator have a fruity fragrance, flowers of 'LIMformosa' have a moderately strong rose fragrance.

2. Flowers of 'Belinda's Dream' have lighter pink petals.
3. Plants of 'Belinda's Dream' are taller than plants of 'LIMformosa'.

Plants of the new cultivar 'LIMformosa' can also be compared to the commercial variety *Rosa* 'Grande Dame', U.S. Pat. No. 20,635. These varieties are similar in most horticultural characteristics, however 'LIMformosa' differs in the following:

1. The new variety has 50 to 80 petals per flower, this comparator has typically 30 petals.
2. Flower buds of 'Grande Dame' are more acutely pointed.
3. Flowers of 'Grande Dame' have a typical rose fragrance, flowers of 'LIMformosa' have a moderately strong rose fragrance.
5. Branching of the new variety is more acute than branching of 'Grande Dame'.

BRIEF DESCRIPTION OF THE PHOTOGRAPH

The accompanying photograph illustrates in full color a close up of an individual flower. The photograph was taken using conventional techniques and although colors may appear different from actual colors due to light reflectance it is as accurate as possible by conventional photographic techniques

DETAILED BOTANICAL DESCRIPTION

In the following description, color references are made to The Royal Horticultural Society Colour Chart 2007 except where general terms of ordinary dictionary significance are used. The following observations and measurements describe 'LIMformosa' plants grown outdoors, in Palm Desert, Calif. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.
Botanical classification: *Rosa* 'LIMformosa'.
Market classification: Shrub.

PROPAGATION

Time to initiate roots: About 15 days at approximately 20° C.
Time to produce a rooted cutting: About 35 days at approximately 20° C.

PLANT

Age of plant described: Approximately 2 years.
Growth habit: Compact spreading.
Container size: 2 gallon.
Height: 50 cm.
Plant spread: 65 cm.
Rootstock: Own root.
Growth rate: Moderate.
Branching characteristics: Sympodial branching.
Length of primary lateral branches: Average 20 cm.
Diameter of lateral branches: Approximately 5 to 7 mm.
Quantity branches: 6 to 8 main branches, moderate lateral branches, 5 to 12 lateral branches per main branch.

Branches-young wood:
*Diameter.*—Approximately 4 mm.
*Texture.*—Glabrous, scant to moderate thorns.
*Approximately density/quantity of thorns.*—Approximately 1 to 2 per linear cm.
*Color.*—Near Green 143C, anthocyanin not observed.

Branches-old wood:
*Diameter.*—Approximately 7 mm.
*Color.*—Near Yellow-Green 144A streaked Greyed-Green 194A.
*Texture.*—Rough thick woody striations.
*Thorns.*—
*Approximately density/quantity of thorns.*—Approximately 4 per linear cm.
*Color of thorns.*—Immature: Near Greyed-Red 181B, base near 185A. Mature: Near Yellow-Green 144D, base 144C.
*Shape.*—Deltoid, slightly hooked.
*Height.*—Average 7 to 9 mm.
*Diameter.*—Base near 5 mm. Tip near 2 mm.

FOLIAGE

Leaf:
*Arrangement.*—Alternate and compound.
*Quantity.*—Average 7 to 12 per main branch.
*Internode.*—Average range 2.5 to 3.8 cm.
*Average length.*—Approximately 7.0 to 9.0 cm.
*Average width.*—Approximately 5.5 cm.

Rachis:
*Average length.*—Approximately 3.5 cm.
*Average diameter.*—Approximately 0.2 cm.
*Color.*—Upper surface: Near RHS Yellow-Green 147A. Lower surface: Near RHS Yellow-Green 144B.
*Texture.*—Glabrous all surfaces. Lower surface may have a small thorn.

Leaflet:
*Quantity.*—5 per leaf, infrequently 7.
*Average length.*—Approximately 3.7 cm.
*Average width.*—Approximately 2.5 cm.
*Shape of blade.*—Ovate.
*Apex.*—Acute.
*Base.*—Rounded.
*Margin.*—Serrate.
*Appearance of top surface.*—Slightly glossy.
*Appearance of bottom surface.*—Matte.
*Texture of top surface.*—Glabrous.
*Texture of bottom surface.*—Glabrous.
*Color.*—Young foliage upper side: Near Yellow-Green 146A, very faint flush near mid vein near Greyed-Red N181B. Young foliage under side: Near Yellow-Green 147B, flushed near Greyed-Red 178A. Mature foliage upper side: Near Green 139A. Mature foliage under side: Near Green 138A.
*Venation.*—Type: Reticulate. Venation color upper side: Near Green 137C. Venation color under side: Near Yellow-Green N144C.

Petiole:
*Average length.*—Approximately 2.0 cm.
*Average diameter.*—Approximately 0.2 cm.
*Color.*—Upper surface: Near Green 137A. Lower surface: Near Yellow-Green 144A.
*Texture.*—Glabrous.

*Petiole wing.*—Typically 8 to 12 mm long and 3 mm wide. Apex Acute or acuminate. Upper surface colored near Green 137A, lower surface colored near Green 137C.

FLOWER

Natural flowering season: Spring until Autumn.

Inflorescence type and habit: Single occurring, fully double rotate flowers.

Rate of flower opening: Approximately 4 days from bud to fully opened flower.

Flower longevity on plant: 7 to 12 days, after fully opened.

Quantity of flowers: 8 to 16 fully opened flowers and buds.

Flower size:

*Diameter.*—Approximately 12 cm.

*Height.*—Approximately 6 cm.

Peduncle:

*Length.*—3 to 5 cm.

*Diameter.*—4 mm.

*Color.*—Near Green 143C flushed Greyed-Red 182A.

Petals:

*Petal arrangement.*—Multiple rotate, overlapping whorls.

*Petal quantity.*—50 to 80.

*Length.*—Average range 4.0 to 5.0 cm.

*Width.*—Average range 1.8 to 3.0 cm.

*Shape.*—Irregular spatulate.

*Margin.*—Entire.

*Apex.*—Rounded, blunt. Occasionally mucronate or very shallow crenations.

*Base.*—Broad attenuate.

*Aspect.*—Moderately upwardly cupped.

*Texture.*—Glabrous all surfaces.

Color: Petals.

*When opening.*—Upper surface: Upper section near Red-Purple 73A, fading to Red-Purple 68B, then 68C. Base near White 155D. Lower surface: Upper 50% near Red-Purple 68B, lightly flushed White 155D in center. Lower section faint margin coloration near 68B, center section White 155D with faint stripes 68C. Base White 155D flushed Yellow 10D.

*Fully opened.*—Upper surface: Upper 75% section near Red-Purple 68A with overall flush of Red-Purple N74C, fading to Red-Purple 68B. Base near Red-Purple 73D flushed 73C. Lower surface: Upper 75% near Red-Purple N74C, very lightly streaked Purple 75D in center. Lower section faint margin coloration near 75D, center section 73D. Base White 155D very faintly flushed Yellow 10D. Color Changes when aging: Upper surface: Upper 75% near Red-Purple N74C, very lightly streaked Purple 75D in center. Lower section faint margin coloration near 75D, center section Purple 75C. Base White 155D. Lower surface: Upper 50% thick margin colored near Purple 75C, center Red-Purple 73D. Lower near Red-Purple 69C. 75D, center section Purple 75C. Base White 155D.

Bud:

*Shape.*—Classic conical rosebud shape.

*Length.*—Approximately 3.5 cm.

*Diameter.*—Approximately 2.5 cm.

*Color.*—Exposed petal colored Near Red-Purple 58D, base near Yellow 5C, streaked Yellow 4D.

Sepals:

*Quantity.*—5.

*Length.*—Average range 3.0 to 3.5 cm.

*Width.*—1.0 cm.

*Shape.*—Narrow deltoid.

*Apex.*—Long, narrow acute.

*Margin.*—Serrate to incised.

*Color.*—Interior Surface: Near Green 138A. Exterior Surface: Near Green 138B.

*Texture.*—Minutely pubescent upper and lower surfaces.

Receptacle:

*Length.*—1.1 cm.

*Width.*—0.7 cm.

*Shape.*—Flattened dome.

*Color.*—Near Green 143D.

Fragrance: Moderately strong, rose fragrance.

REPRODUCTIVE ORGANS

Stamens:

*Quantity.*—Average range 40 to 60.

*Filament length.*—Approximately 1.0 to 1.3 cm.

*Filament color.*—Near Yellow 4D.

Anthers:

*Length.*—2 mm.

*Shape.*—Elliptic.

*Color.*—Near Greyed-Orange 172C.

*Pollen.*—Color: Greyed-Orange 172D. Quantity: Scant.

Pistil: Somewhat malformed. Tightly attached and densely packed vertically to receptacle.

*Number.*—Approximately 10 to 30.

*Pistil length.*—Approximately 8 mm.

*Style.*—Length: Approximately 5 mm. Color: Near Yellow-Green 144C.

*Stigma.*—Shape: Linear. Color: Near Yellow-Green 144D.

*Ovary color.*—Near Yellow-Green 144D.

*Ovary shape.*—Flat oblong.

*Ovary length.*—Average 3 mm.

*Ovary diameter.*—Average 2 mm.

OTHER CHARACTERISTICS

Seeds and fruits: Not observed.

Disease/pest resistance: Strongly resistant to black spot. Good resistance to normal pests and diseases typical of garden roses.

What is claimed is:

1. A new and distinct shrub rose cultivar plant named 'LIMformosa' as herein illustrated and described.

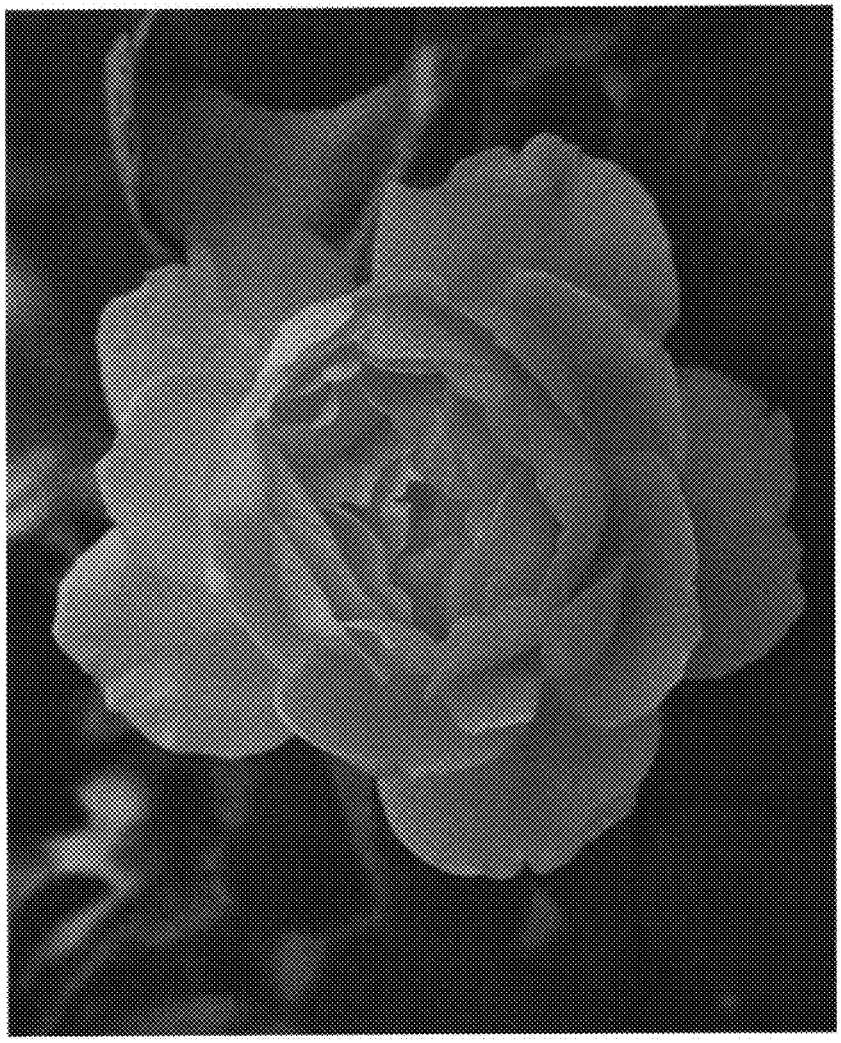

* * * * *